United States Patent
Taylor et al.

(10) Patent No.: US 10,706,744 B2
(45) Date of Patent: Jul. 7, 2020

(54) PENILE PROSTHESIS DEMONSTRATION TOOL

(71) Applicant: Coloplast A/S, Humlebaek (DK)

(72) Inventors: Jeffrey Brian Taylor, Forest Lake, MN (US); Shannon Tufvander, Maple Plain, MN (US)

(73) Assignee: Coloplast A/S, Humlebaek (DK)

( * ) Notice: Subject to any disclaimer, the term of this patent is extended or adjusted under 35 U.S.C. 154(b) by 292 days.

(21) Appl. No.: 15/922,936

(22) Filed: Mar. 16, 2018

(65) Prior Publication Data

US 2019/0287424 A1 Sep. 19, 2019

(51) Int. Cl.
- G09B 23/28 (2006.01)
- G09B 23/32 (2006.01)
- G09B 9/00 (2006.01)
- A61F 2/26 (2006.01)

(52) U.S. Cl.
CPC ............... *G09B 23/32* (2013.01); *A61F 2/26* (2013.01); *G09B 9/00* (2013.01)

(58) Field of Classification Search
USPC ..... 434/262, 267, 268, 272, 273; 600/38–40
See application file for complete search history.

(56) References Cited

U.S. PATENT DOCUMENTS

| | | | | |
|---|---|---|---|---|
| 4,267,829 A | * | 5/1981 | Burton | A61F 2/26 600/40 |
| 5,899,849 A | * | 5/1999 | Elist | A61F 2/26 128/898 |
| 6,060,639 A | | 5/2000 | Petrick | |
| 7,407,482 B2 | * | 8/2008 | Kuyava | A61F 2/26 600/40 |
| 8,641,423 B2 | * | 2/2014 | Gumkowski | G09B 23/34 434/262 |
| 8,764,629 B2 | * | 7/2014 | Braud | A61F 5/41 600/39 |
| 2008/0032274 A1 | * | 2/2008 | Isaacs | G09B 23/28 434/268 |
| 2011/0091855 A1 | * | 4/2011 | Miyazaki | G09B 23/281 434/267 |
| 2016/0081801 A1 | * | 3/2016 | Little | A61F 2/26 600/40 |
| 2018/0064536 A1 | | 3/2018 | Brown et al. | |
| 2019/0000626 A1 | * | 1/2019 | Tal | A61F 2/26 |
| 2019/0091025 A1 | * | 3/2019 | Lund | A61F 2/26 |

FOREIGN PATENT DOCUMENTS

| | | |
|---|---|---|
| EP | 3141220 A1 | 3/2017 |
| WO | 2007073556 A2 | 6/2007 |
| WO | 2009132657 A1 | 11/2009 |
| WO | 2011050031 A1 | 4/2011 |

* cited by examiner

*Primary Examiner* — Kurt Fernstrom (74) *Attorney, Agent, or Firm* — Coloplast Corp., Coloplast A/S; Nick Baumann (57) ABSTRACT

A penile prosthesis demonstration tool includes a male genital tool connected to an exterior of the housing. The housing has a first lateral side and an opposing second lateral side, with the first lateral side and the second lateral side each formed to have a concave curvature. The male genital tool has a penis tool attached to a scrotum tool. An inflatable penile implant placed inside of the penis tool; a pump placed inside of the scrotum tool and coupled to the inflatable penile implant; a reservoir placed inside of the housing and coupled to the pump; and a lubricant placed inside of the scrotum tool. An entirety of the lubricant outside of the pump.

12 Claims, 9 Drawing Sheets

PENILE PROSTHESIS DEMONSTRATION TOOL

BACKGROUND

Implantable penile prostheses have offered men experiencing erectile dysfunction an ability to have an erection that is suitable for penetrative intercourse. The implantable penile prostheses include a pump connected to a reservoir and a pair of inflatable penile prostheses. Some men have difficulty manipulating the pump, where due to dexterity or a lack of practice with the pump. Surgeons who have advised such patients have come to realize that some patients are tentative in how they handle the newly implanted penile prosthetic, and other patients have been observed using a sub-optimal approach to actuating the pump of the newly implanted penile prosthetic. Surgeons and patients would both welcome an opportunity for the patient to become familiarized with the function of an implanted penile prosthetic in a clinical setting.

SUMMARY

One aspect provides a penile prosthesis demonstration tool includes a male genital tool connected to an anterior face of a housing. The anterior face of the housing extends between a first lateral side, a second lateral side, a superior top side, and an inferior bottom side. The male genital tool includes a penis tool attached to a scrotum tool, with an inflatable penile implant placed inside of the penis tool, a pump placed inside of the scrotum tool and coupled to the inflatable penile implant, a lubricant placed inside of the scrotum tool and located between an interior wall of the scrotum tool and an exterior of the pump, and a reservoir placed inside of the housing and coupled to the pump. The pump is operable to move a liquid contained in the reservoir into the inflatable penile implant to simulate an erection in the penis tool. The demonstration tool allows a surgeon to coach a person with an implanted penile prosthetic on the operation and expected function and response of the implant in a comfortable office setting without fear of causing pain or damaging the actual implant.

Embodiments of the penile prosthesis demonstration tool provide each of the first lateral side and the second lateral side with a concave curvature, which advantageously allows the housing to be secured in a comfortable manner between the interior thighs of the user to allow the user to focus on the demonstration tool instead of a discomfort.

Embodiments of the penile prosthesis demonstration tool provide each of the superior top side and an inferior bottom side with a convex curvature. The convex superior top side is adapted to comfortably meet with the user's mid-section. In one embodiment, the inferior bottom side is planar or flat to be adapted to rest upon a seat of a chair.

Embodiments of the penile prosthesis demonstration tool provide the male genital tool with a base having a first portion inserted into the anterior face of the housing and a second portion located between the anterior face of the housing and the scrotum tool. These features securely connect the male genital tool to the housing in an anatomically appropriate representation of the human male.

Embodiments of the penile prosthesis demonstration tool provide a siloxane lubricant that is highly slippery to accurately reflect the slippage that occurs between the pump and the skin of the scrotum in an actual implanted prosthetic.

Embodiments of the penile prosthesis demonstration tool provide a silicone oil lubricant that is affordable and highly slippery.

Embodiments of the penile prosthesis demonstration tool include a dimethicone lubricant, which advantageously has been found to closely mimic the slippage that occurs between the pump and the skin of the scrotum in an actual implanted prosthetic.

Embodiments of the penile prosthesis demonstration tool provide a non-toilet soap lubricant, which is affordable, highly slippery, and widely available.

Embodiments of the penile prosthesis demonstration tool provide a toilet soap lubricant, which is affordable, highly slippery, and widely available.

Embodiments of the penile prosthesis demonstration tool provide a mineral oil lubricant that is both slippery and widely available.

One aspect provides a penile prosthesis demonstration tool including a housing having a first lateral side and an opposing second lateral side, with the first lateral side and the second lateral side each formed to have a concave curvature; a male genital tool connected to an exterior of the housing, the male genital tool including a penis tool attached to a scrotum tool; an inflatable penile implant placed inside of the penis tool; a pump placed inside of the scrotum tool and coupled to the inflatable penile implant; a reservoir placed inside of the housing and coupled to the pump; and a lubricant placed inside of the scrotum tool, with an entirety of the lubricant outside of the pump. The demonstration tool allows a surgeon to coach a person with an implanted penile prosthetic on the operation and expected function and response of the implant in a comfortable office setting without fear of causing pain or damaging the actual implant.

Embodiments of the penile prosthesis demonstration tool provide the concave curvature of the first lateral side and the second lateral side sized to allow the housing to be positioned between adductor muscles of legs at an inner thigh location of a user. These features allow the housing to sit comfortably near the groin of the clothed user.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following detailed description, reference is made to the accompanying drawings. The drawings form a part of this specification and illustrate exemplary embodiments for practicing the invention. Directional terminology, such as "top," "bottom," "front," "back," "leading," "trailing," etc., is used with reference to the orientation of the Figure(s) being described. Because components of embodiments can be positioned in a number of orientations, the directional terminology is used for purposes of illustration and is in no way limiting. It is to be understood that other embodiments may be utilized and structural or logical changes may be made without departing from the scope of the invention. The detailed description describes examples for practicing the invention and is not to be read to limit the scope of the invention. The scope of the invention is defined by the attached claims.

End means endmost. Relative to an observer, for example a surgeon, a distal end is the furthest endmost location of a distal portion of a thing being described, whereas a proximal end is the nearest endmost location of a proximal portion of the thing being described. The portion next to or adjacent to an end is an end portion.

An implanted penile prosthesis has proven useful in treating erectile dysfunction in men. One acceptable implanted penile prosthesis includes two inflatable cylinders implanted in the penis, a pump implanted in the scrotum or other internal space of the body, and a liquid holding reservoir implanted in the abdomen or other internal space of the body, with the pump connected to the cylinders and the reservoir.

In an implantation procedure, the penis of the patient is incised in a corporotomy to expose a pair of corpora cavernosa that are aligned axially in a side-by-side orientation within the penis. A cutting implement, such as a curved Mayo scissors, is employed to penetrate the fascia of the penis and form an opening accessing each corpora cavernosum. Subsequently, each corpora cavernosum is dilated (opened) with an appropriate dilation tool to form a recess that is sized to receive one of the two cylinders of the penile prosthesis.

Thereafter, a tool (referred to by surgical practitioners as a "Furlow" introducer) is inserted into each dilated corpora cavernosum to measure a length of the penis distally and proximally to determine a desired length of the cylinders to be implanted. A cylinder of the appropriately measured length is secured to a suture, and the suture is secured to a needle (sometimes called a "Keith" needle). The Keith needle is attached to the Furlow introducer, which is employed to push the Keith needle through tissue of the penis and out the glans penis. The suture attached to the Keith needle and to the cylinder is subsequently employed to tow the cylinder into place within the dilated corpora cavernosum.

A reservoir holding a volume of liquid is implanted into an abdominal space, and a pump for moving the liquid in the reservoir is implanted into the scrotum. Suitable connections are made to fluidly connect the pump in the scrotum to the reservoir in the abdomen and to the cylinders in the penis.

The patient heals over a period of weeks prior to activating the pump and creating an erection in the penis for the first time. Some patients are hesitant to assertively squeeze a pump bulb of the pump, and consequently have difficulty in fully inflating the penile implant with liquid from the reservoir. Surgeon and patients would both benefit by having a demonstration tool that would allow the surgeon to demonstrate to the patient how best to actuate the pump in creating an erection with the penile prosthetic.

Currently, a prospective patient has an opportunity to view the implantable prosthesis while in the surgeon's office prior to the implantation. The patient can clearly see the location of the pump bulb and even see the passage of liquid during pumping when the prosthesis is ex vivo. However, when the pump is implanted, the pump bulb is located between the testicles within the scrotum and can be difficult to locate and grasp. Even when located, the pump bulb tends to slip from between the fingers when the patient is attempting to actuate the implanted prosthetic. While the pump and the prosthetic work in the same manner whether ex vivo or implanted, the patient's experience with the device changes after implantation, in part due to inexperience with operating the pump bulb or a hesitancy to fully engage the pump bulb. The demonstration tool disclosed in this application provides the same prosthesis within a realistic tool of a penis and scrotum to allow the user to practice overcoming the challenge of the slippery pump bulb. In addition, the housing of the demonstration tool is structured to be placed between the thighs of the user, near the groin, to realistically mimic the location of an implanted penile prosthetic. Thus, the user (before receiving a penile prosthetic or after implantation of the prosthesis) can practice while clothed in the surgeon's office on a realistic tool that is located near the groin. The user is able to familiarize themselves with the operation of an implanted prosthetic by using the demonstration tool, and can thus overcome the challenges that some patients experience when attempting to inflate the prosthetic. Surgeons benefit by having a more informed and confident patient, which results in an overall more positive implantation experience.

Embodiments provide a penile prosthesis demonstration tool that allows surgeons and patients to become familiarized with the function of an implanted penile prosthetic by practicing with the demonstration tool in a clinical setting.

Embodiments provide a penile prosthesis demonstration model that allows surgeons and patients to become familiarized with the function of an implanted penile prosthetic by practicing with the demonstration model in a clinical setting.

Figure 1:
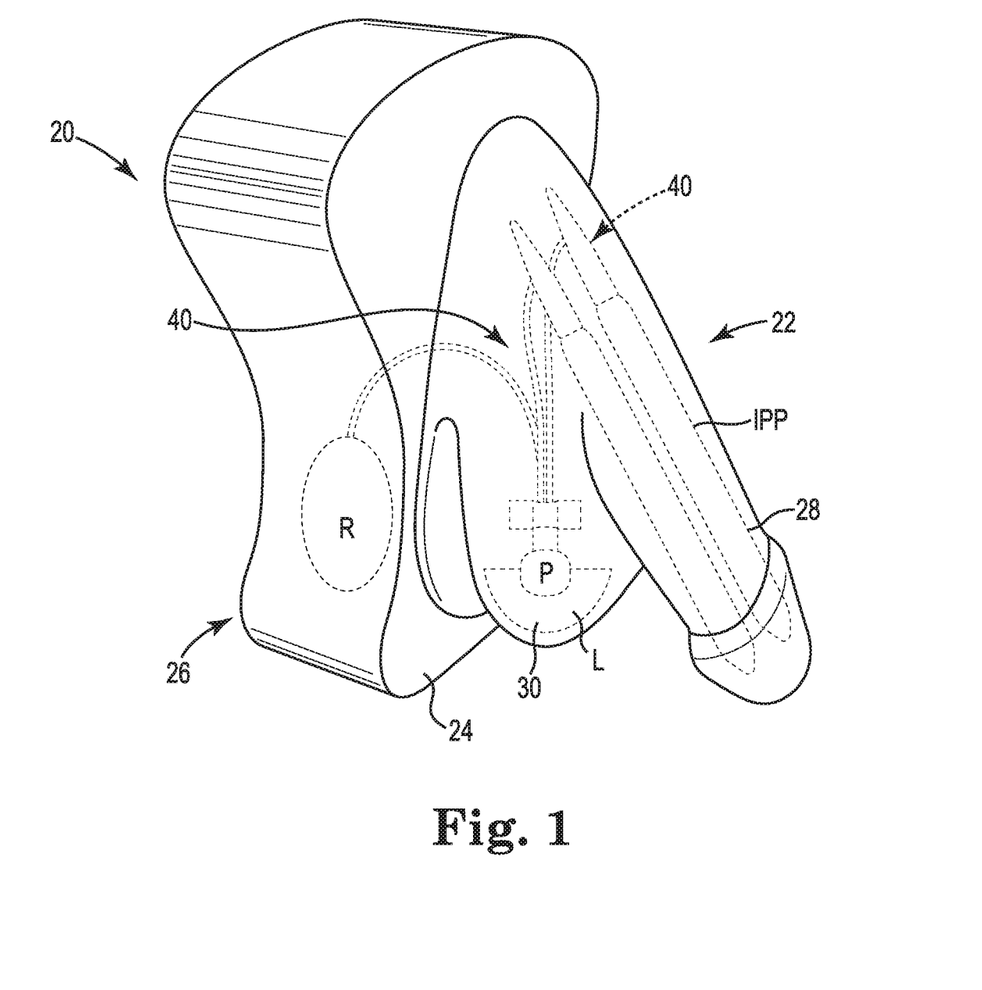
FIG. 1 is a perspective view of one embodiment of a penile prosthesis demonstration tool.

FIG. 1 is a perspective view of one embodiment of a penile prosthesis demonstration tool 20. The demonstration tool 20 includes a male genital tool 22 connected to an anterior face 24 of a housing 26. The male genital tool 22 includes a penis tool 28 that is attached to a scrotum tool 30. The male genital tool 22 is formed of a polymer to provide a life-like representation of human skin.

The housing 26 is adapted to be captured or secured between the legs of a patient or user, and a pump located in the scrotum tool 30 is operable to move the penis tool 28 between a flaccid state and an erect state. The demonstration tool 30 allows a surgeon to coach a person with an implanted penile prosthetic on the operation and expected function and response of the implant. The user can practice while clothed in the surgeon's office on a realistic tool that is located near the groin. The user, even before implantation of a prosthesis, can familiarize themselves with the operation of an implanted prosthetic by using the demonstration tool. For example, the user sits on a chair in the surgeon's office and places the housing 26 between the thighs and as near to the groin as is comfortable. The scrotum tool 30 realistically tools a male scrotum and allows the user to get a feel for locating and actuating the pump bulb. Alternatively, the user, after implantation of the prosthesis, can practice on the demonstration tool to overcome the challenges that are presented when inflating an implanted prosthetic. Locating the housing 26 near the groin and providing realistic penis and scrotum tools allows the patient to practice the actions that they will later take to inflate their own implanted prosthetic.

Suitable polymers for the exterior of the male genital tool 22 include pigmented polyurethane or silicone having skin tone color. The skin color is selected as a tone having a brightness on the CIE L*a*b* color scale, where the brightness L* has a range from L*=0 for black to L*=100 for white, a* ranges from negative values for green to positive values for red, and b* ranges from negative values for blue to positive values for yellow. One may select a desired skin tone by selecting a color from the color spectrum chart of the CIE L*a*b* color scale.

An implant 40 is placed inside of the male genital tool 22, where the implant 40 includes an inflatable penile implant IPP placed inside of the penis tool 28, a pump P placed inside of the scrotum tool 30, and a reservoir R placed inside of the housing 26. A lubricant L is placed inside of the scrotum tool 30 between an interior wall of the scrotum tool 30 and an exterior of the pump P. The pump P is operable to move a liquid that is contained in the reservoir R into the inflatable penile implant IPP to simulate an erection in the penis tool 28. The lubricant L is provided inside of the scrotum tool 30 to replicate the sliding that occurs between the pump P and skin of the scrotum when actuating an actual implanted penile prosthetic. The demonstration tool 20 is a reusable teaching tool that allows the surgeon to show a patient having a new penile prosthetic how to squeeze the pump bulb while overcoming the tendency of the bulb to slide and move within the scrotum.

Figure 2A:
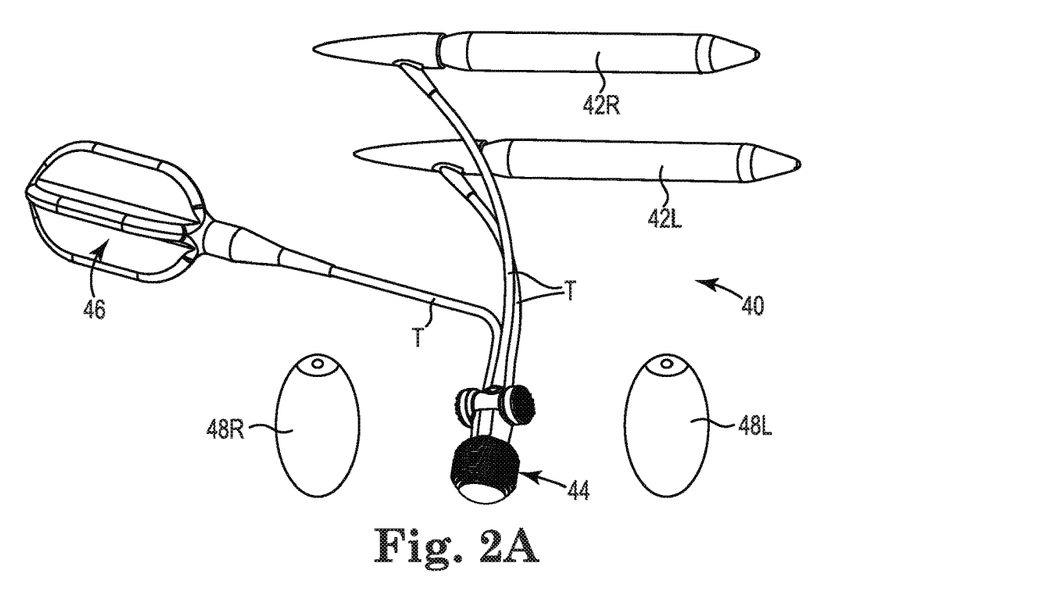
FIG. 2A is a perspective view of one embodiment of components of a penile implant.
Figure 2B:
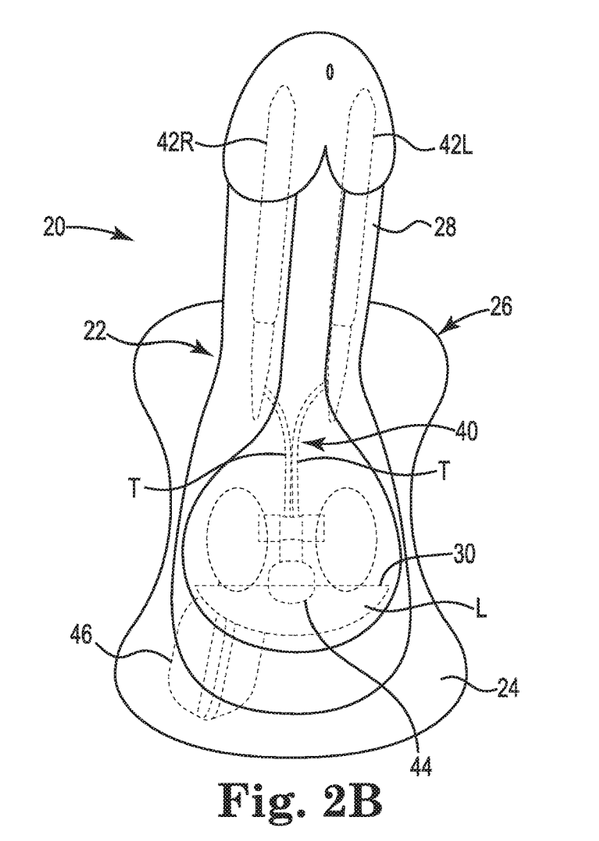
FIG. 2B is a front view of the demonstration tool illustrated in FIG. 1 incorporating the components illustrated in FIG. 2A.

FIG. 2A is a perspective view of components of the implant 40, and FIG. 2B is a front view of the demonstration tool 20 including a schematic of a location of the implant 40.

The components of the implant 40 include a first inflatable penile implant 42L, a second inflatable penile implant 42R, a pump 44, a reservoir 46, and tubing T provided to attach the first and second inflatable penile implants 42L, 42R to the reservoir 46 and the pump 44. The first and second inflatable penile implants 42L, 42R are placed within the respective left and right hand sides of the penis tool 28. The pump 44 is placed inside of the scrotum tool 30 along with the lubricant L. It is desirable to seal the lubricant L inside of the scrotum tool 30 to prevent leakage of the lubricant outside of the demonstration tool 20. The reservoir 46 is placed inside of the housing 26.

One suitable example of the implant 40 is the Titan® inflatable penile implant available from Coloplast Corp., Minneapolis, Minn.

The lubricant L is placed inside of the scrotum tool 30 to simulate slippage that occurs between an implanted pump and the skin of the scrotum in an actual user. In one embodiment, a left 48L and a right 48R testicular prosthesis is provided and placed inside of the scrotum tool 30 along with the lubricant L in the pump 44. One suitable example of testicular prostheses is the Torosa® testicular prostheses available from Coloplast Corp., Minneapolis, Minn.

The lubricant L is provided as a slip aid inside of the scrotum tool 30. Suitable lubricants include wet, or liquid, lubricants and dry lubricants. Suitable examples of wet lubricants include siloxane, silicone oil, dimethicone, a non-toilet soap, a toilet soap, or a mineral oil. Suitable examples of dry lubricants include graphite or molybdenum disulfide.

As noted above, the patient often will handle an example of the penile prosthesis prior to implantation, and the patient will find that manipulating the pump bulb is an easy endeavor with the implant ex vivo, in part because the bulb is visible and easy to grasp. However, the patient generally will have no experience with actuating the pump bulb after implantation. After implantation, the user will come to realize that the pump bulb is free to move within the scrotum and is difficult to discern and difficult to grasp. The implanted pump bulb is difficult to grasp because it is located between the testes, and the scrotum will have hydrated tissue and fluid that causes the implanted pump bulb to slip around inside of the scrotum. The lubricant L causes the pump 44 inside of the scrotum tool 30 to slide around when squeezed, which accurately reflects the real-life experience of an implanted pump inside of a male scrotum. If the lubricant L is not placed inside of the scrotum tool 30, then the pump 44 will have a substantial level of friction when moving inside of the scrotum tool 30, which makes the pump 44 unrealistically easy to grasp with the thumb and forefingers. The dimethicone lubricant inside of the scrotum tool 30 has been found to advantageously and accurately represent the slipperiness of a pump relative to a human scrotum. The combination of the demonstration tool 30 being adapted for placement between the thighs with the realistic slipperiness of the pump 44 inside of the scrotum tool 30 provided by the lubricant has been determined to be an excellent proximation of the challenges that a user will experience with his own implanted prosthetic.

Siloxane is a functional group having an Si—O—Si linkage. One specific siloxane as a branched compound where each pair of the Si centers is separated by one oxygen atom. One example of a siloxane is polydimethylsiloxane, which is referred to as dimethicone. A silicone oil is any liquid polymerized siloxane having organic side chains, examples of which include dimethicone or hexamethyldisiloxane. Thus, one suitable lubricant L is dimethicone which, when placed inside of the scrotum tool 30, provides a life-like representation of slippage for a pump implanted inside of a scrotum.

A soap is a salt of a fatty acid. A non-toilet soap is an emulsion of a soap, usually a metal soap like calcium or lithium, and an oil. One example of a non-toilet soap is a lubricating grease.

A toilet soap is a particular form of soap having an insoluble fat molecule inside of a micelle. Micelles are small spheres formed from soap molecules with polar hydrophilic groups on the outside surrounding a lipophilic pocket. The polar hydrophilic group shields the fat molecule from water, and the lipophilic pocket is soluble in water, which allows the soap to be ultimately soluble in water. Both toilet soaps and non-toilet soaps are useful as a slip aid inside of the scrotum tool 30.

Mineral oil is a term used to describe a transparent, colorless oil composed of alkanes and cycloalkanes. Mineral oil, sometimes called white mineral oil, is useful as a slip aid inside of the scrotum tool 30.

A dry lubricant such as molybdenum disulfide is useful as a slip aid inside of the scrotum tool 30.

Figure 3:
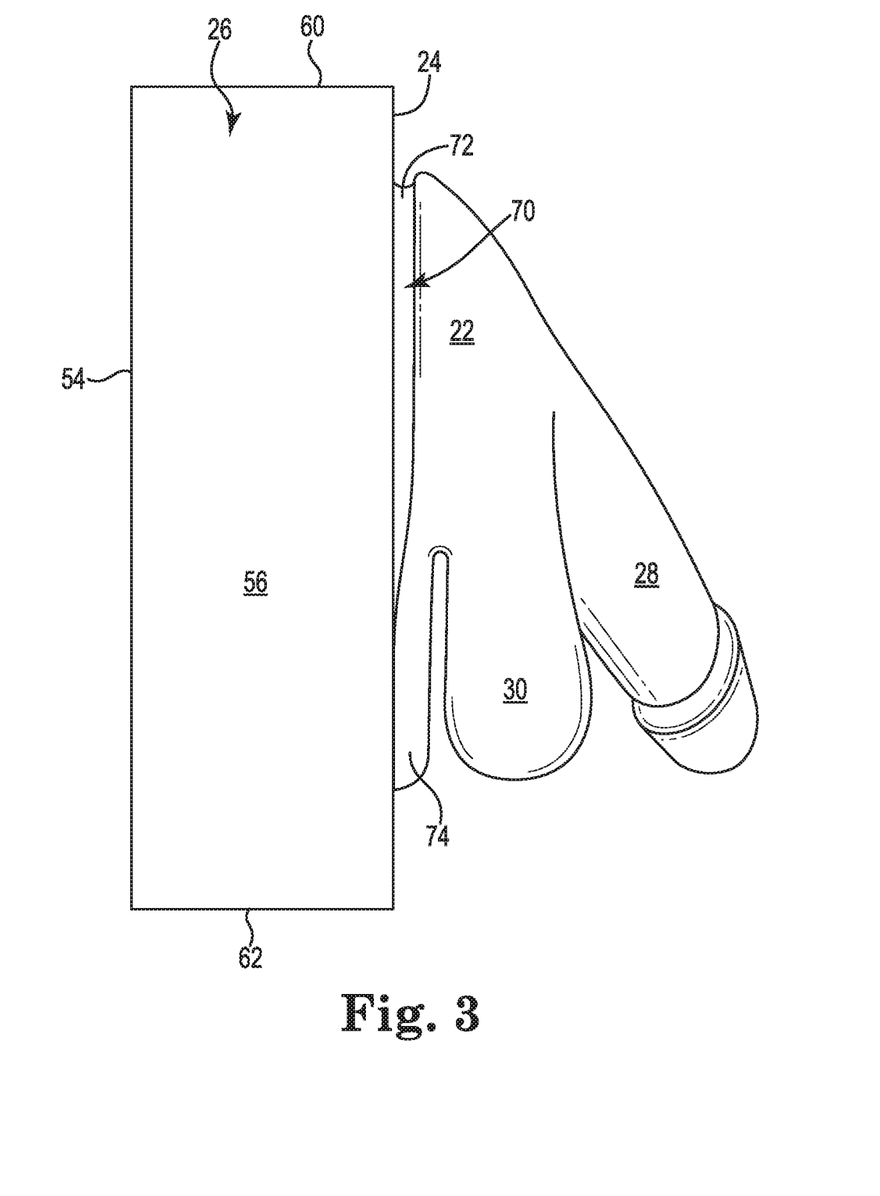
FIG. 3 is a left side view of the demonstration tool illustrated in FIG. 1.
Figure 4:
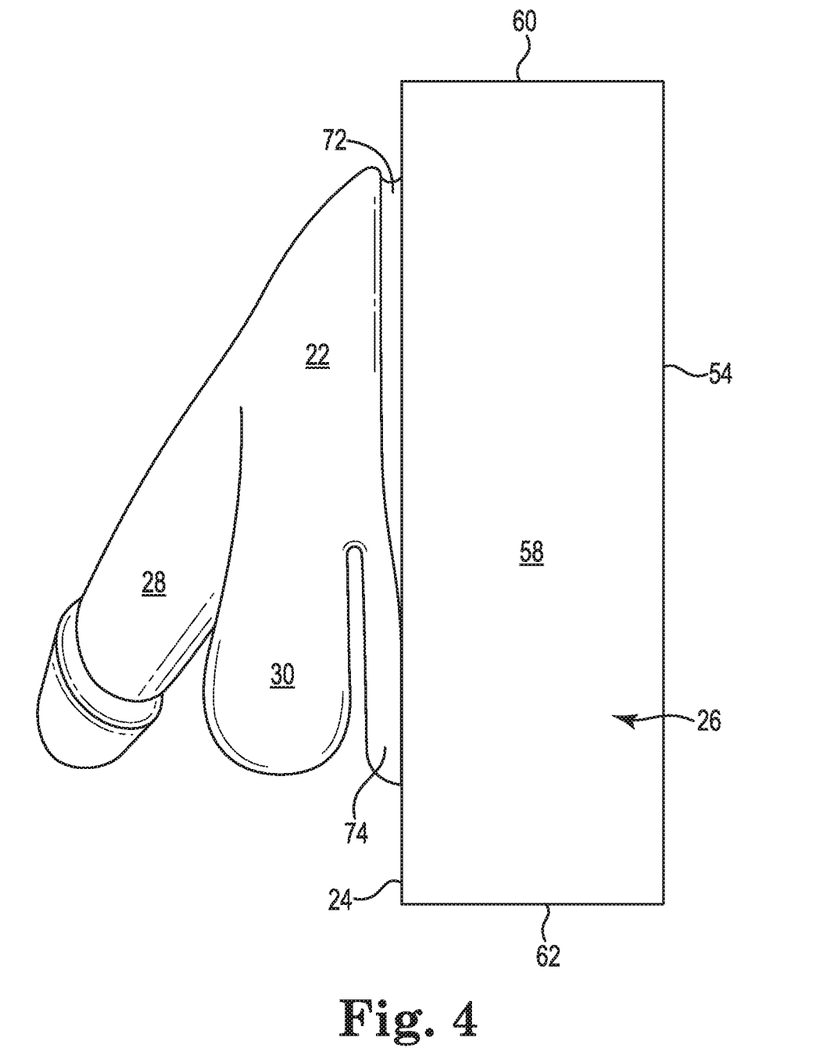
FIG. 4 is a right side view of the demonstration tool illustrated in FIG. 1.
Figure 5:
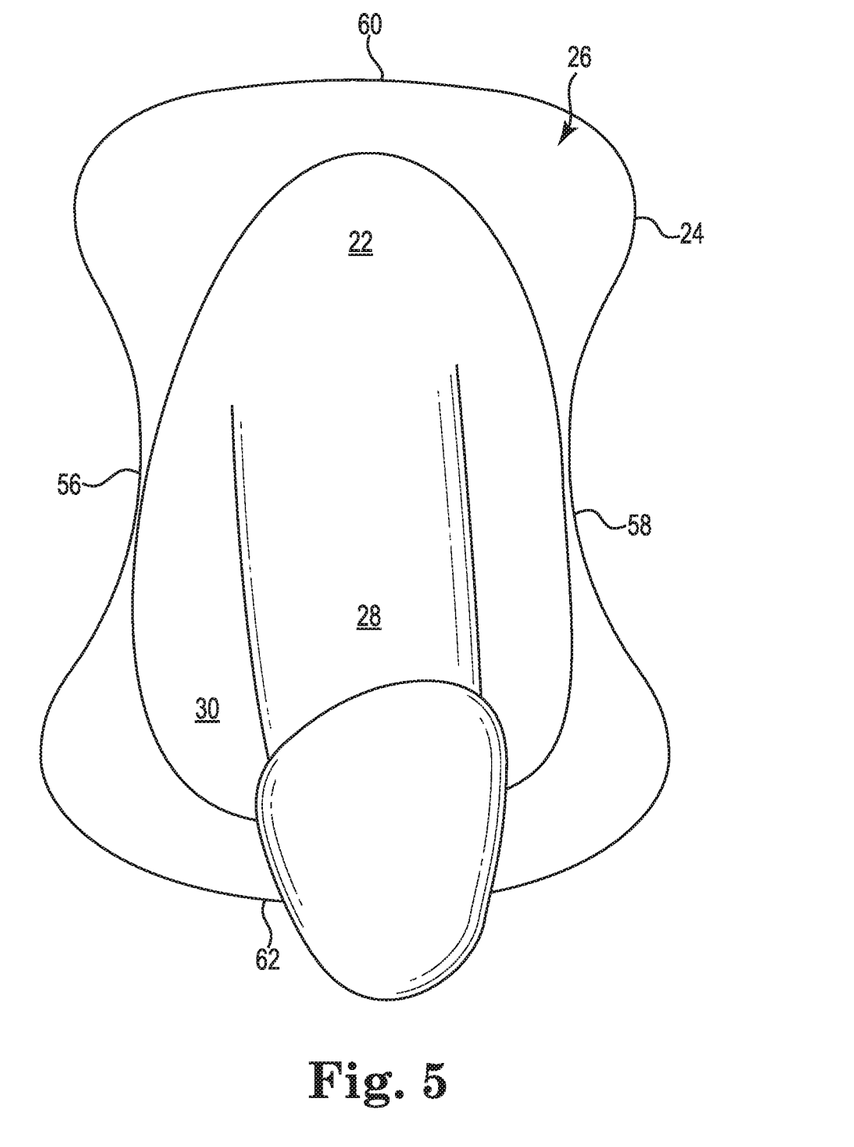
FIG. 5 is a front view of the demonstration tool illustrated in FIG. 1.

FIG. 3 is a left side view, FIG. 4 is a right side view, and FIG. 5 is a front view of the demonstration tool 20. The housing 26 of the demonstration tool includes a posterior face 54 opposite of the anterior face 24, a first lateral side 56 opposite from a second lateral side 58, and a superior topside 60 that is opposite from an inferior bottom side 62. The housing 26 is a three-dimensional structure that is sized to support the male genital tool 22 and provide a cavity between the anterior face 24 and the posterior face 54 for storage of the reservoir 46 (FIG. 2A).

In one embodiment, the posterior face 54 is removable from the housing 26 to provide access to the cavity into the reservoir 46.

In one embodiment, each of the first lateral side 56 and the second lateral side 58 has a concave curvature. The convexity of the concave curvature of the first and second lateral sides 56, 58 is sized to allow the housing 26 to be positioned between adductor muscles of legs at an inner thigh location of a user. The adductor muscles of the inner thigh extend from the pelvis at a location near the perineum down to a midpoint of the thigh. Thus, the concavity of the first and second lateral sides 56, 58 is sized to form a depression to accommodate the typical or average or usual diameter of the thigh of a male at a location near the groin, or more specifically, the perineal skin area.

In one embodiment, each of the superior topside 60 and the inferior bottom side 62 is shaped to have a convex curvature. The housing 26 is to be located near the groin, usually while the user is seated on a chair. It is acceptable to have a flat, planar surface for the inferior bottom side 62 of the housing 26, which allows the housing 26 to rest on the seat of the chair during the demonstration.

In one embodiment, the male genital tool 22 includes a base 70 that is secured to the anterior face 24 of the housing 26. The base 70 includes a first portion 72 that is inserted into an opening in the anterior face 24 of the housing 26, and a second portion 74 that is located between the anterior face 24 in the scrotum tool 30.

Figure 6:
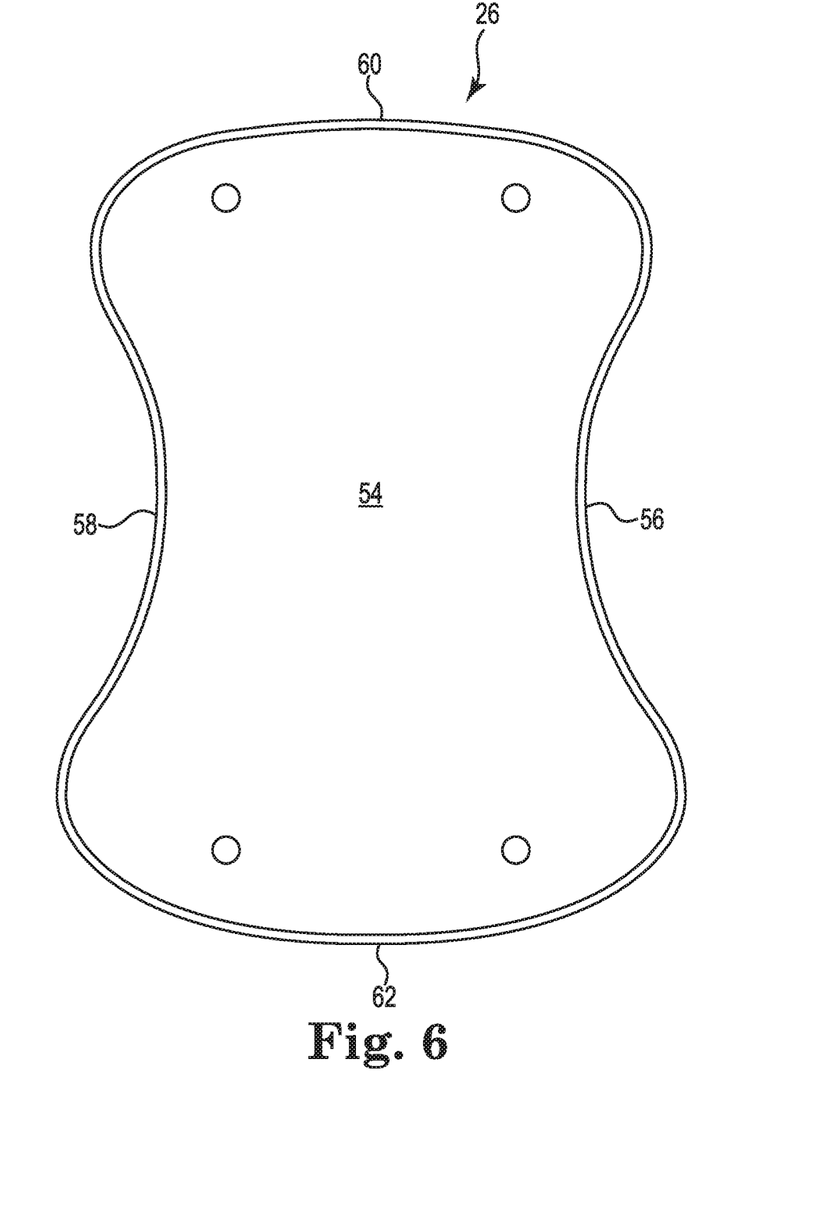
FIG. 6 is a back side view of the demonstration tool illustrated in FIG. 1.
Figure 7:
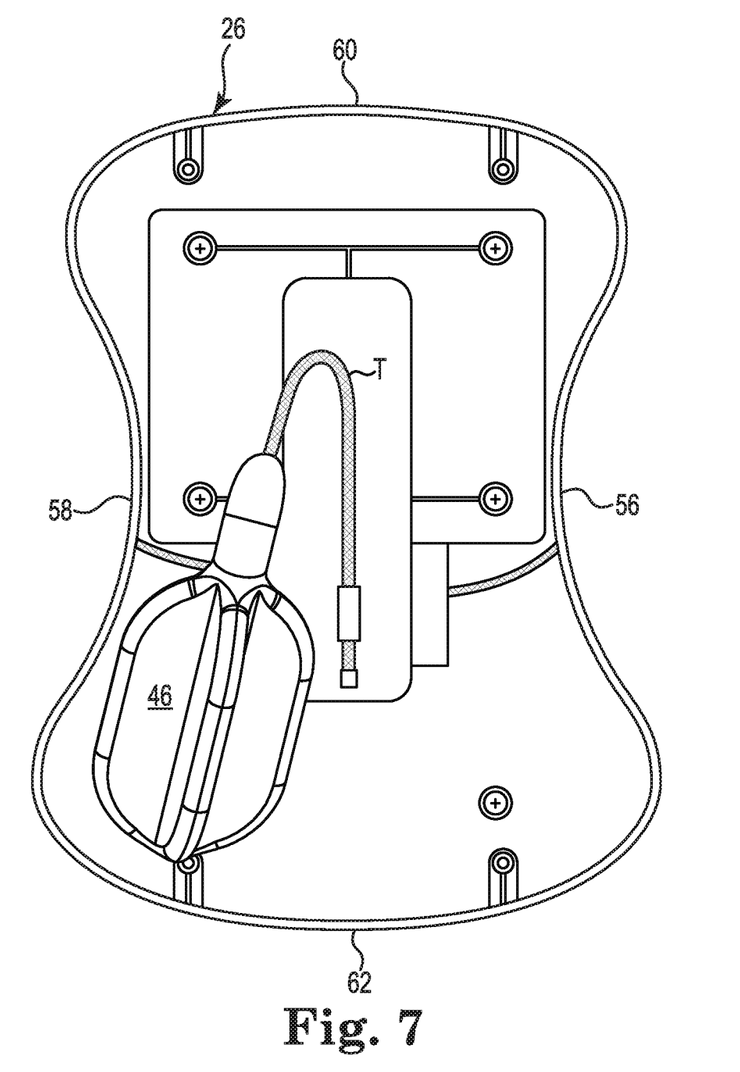
FIG. 7 is a view of an interior of a housing of the demonstration tool illustrated in FIG. 1.

FIG. 6 is a backside view of the housing 26, and FIG. 7 is a view of the posterior face 54 removed from the housing 26. In one embodiment, the posterior face 54 is molded as an insert to fit between the first and second lateral sides 58, 56 and the superior topside 60 and the inferior bottom side 62. The posterior face 54 is attached to the housing 26 with a suitable connector, for example with glue, screws, or a snap fit connection. Removal of the posterior face 54 exposes the reservoir 46 and the tubing T that connects the reservoir 46 to the pump 44.

Figure 8:
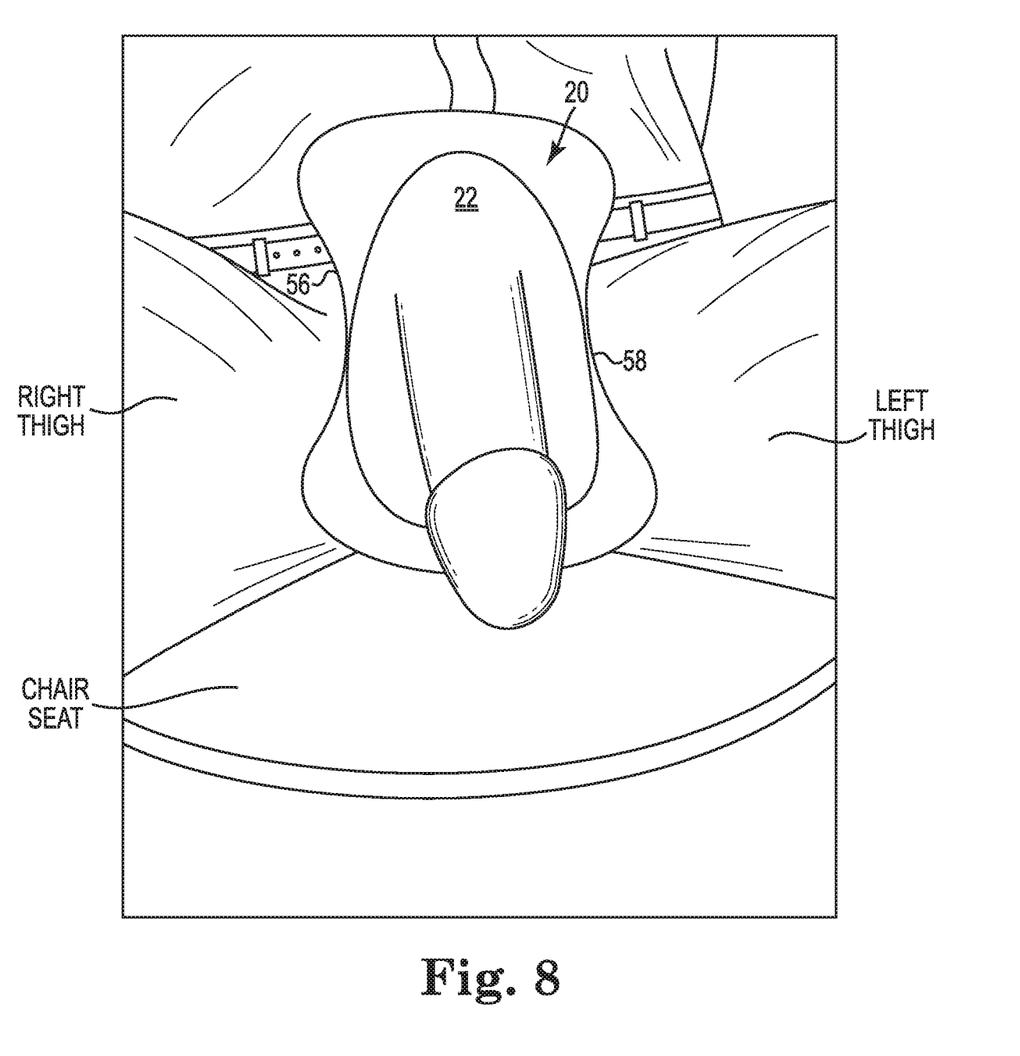
FIG. 8 is a front view of the demonstration tool positioned between adductor muscles of legs at an inner thigh location of a user.

FIG. 8 is a front view of the demonstration tool 20 positioned between adductor muscles of legs at an inner thigh location of a user. Occasionally, a patient with a penile implant will experience difficulties in manipulating the pump to achieve an erection or in manipulating the release valve to return to the flaccid state. The demonstration tool 20 allows the surgeon to instruct the patient on the proper use of the penile implant. The surgeon will have the patient sit on a chair with the demonstration tool 20 located between the thighs at a location as close to the groin as is comfortable for the clothed user. The concave surface of the first lateral side 56 accommodates and curves around the inner thigh of the right leg, while the concave surface of the second lateral side 58 accommodates and curves around the inner thigh of the left leg. The inferior bottom side 62 of the demonstration tool 20 rests upon the seat of the chair. The surgeon will show the patient how to effectively grasp and operate the pump 46 located within the scrotum tool 30 to achieve an erection in the demonstration tool 20. The lubricant L will cause the pump 46 to slide relative to the scrotum tool 30 and the testicular prostheses, which mimics the natural environment of an actual penile implant. The patient will gain experience and competence in the use of the penile implant through practice with the demonstration tool 20.

Figure 9:
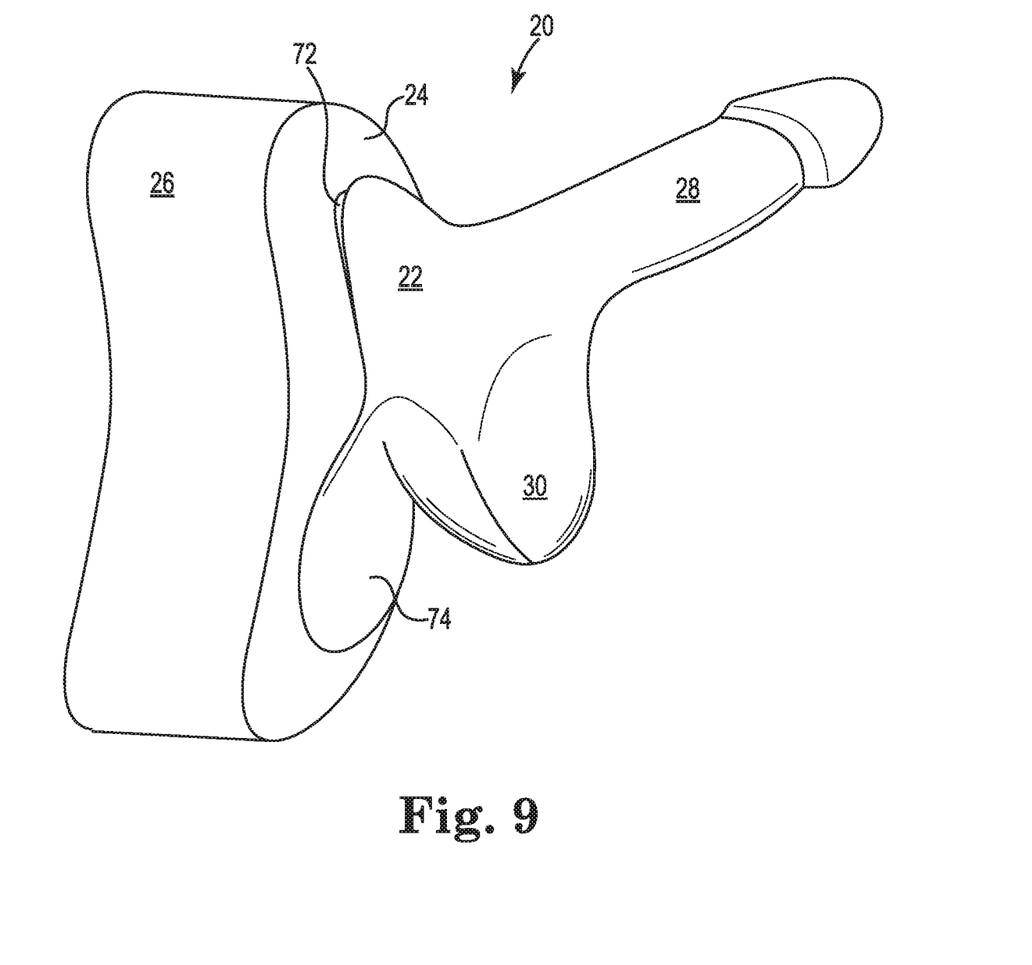
FIG. 9 is a perspective view of one embodiment of the penile prosthesis demonstration tool with the penis tool in an erect state.

FIG. 9 is a perspective view of one embodiment of the penile prosthesis demonstration tool 20 with the penis tool 28 in an erect state. The first portion 72 of the base connects the male genital tool 22 to the housing 26. The second portion 74 of the base is integrated with the scrotum tool 30 to provide a representation of the groin.

Although specific embodiments have been illustrated and described, it will be appreciated by those of ordinary skill in the art that a variety of alternate and equivalent implementations may be substituted for the specific embodiments shown and described without departing from the scope of the present invention. This application is intended to cover any adaptations or variations of the kind of medical devices described above. Therefore, it is intended that this invention be limited only by the claims and their equivalents.

What is claimed is:

1. A penile prosthesis demonstration tool comprising:
a housing having an anterior face extending between a first lateral side, a second lateral side, a superior top side, and an inferior bottom side;
a male genital tool including a penis tool attached to a scrotum tool, with the male genital tool connected to the anterior face of the housing;
an inflatable penile implant placed inside of the penis tool;
a pump placed inside of the scrotum tool and coupled to the inflatable penile implant;
a lubricant placed inside of the scrotum tool and located between an interior wall of the scrotum tool and an exterior of the pump; and
a reservoir placed inside of the housing and coupled to the pump;
wherein the pump is operable to move a liquid contained in the reservoir into the inflatable penile implant to simulate an erection in the penis tool.

2. The penile prosthesis demonstration tool of claim 1, wherein each of the first lateral side and the second lateral side has a concave curvature.

3. The penile prosthesis demonstration tool of claim 1, wherein each of the superior top side and an inferior bottom side has a convex curvature.

4. The penile prosthesis demonstration tool of claim 1, wherein the male genital tool includes a base, with a first portion of the base inserted into the anterior face of the housing and a second portion of the base is located between the anterior face of the housing and the scrotum tool.

5. The penile prosthesis demonstration tool of claim 1, wherein the lubricant is a siloxane.

6. The penile prosthesis demonstration tool of claim 1, wherein the lubricant is a silicone oil.

7. The penile prosthesis demonstration tool of claim 1, wherein the lubricant is dimethicone.

8. The penile prosthesis demonstration tool of claim 1, wherein the lubricant is a non-toilet soap.

9. The penile prosthesis demonstration tool of claim 1, wherein the lubricant is a toilet soap.

10. The penile prosthesis demonstration tool of claim 1, wherein the lubricant is a mineral oil.

11. A penile prosthesis demonstration tool comprising:
- a housing having a first lateral side and an opposing second lateral side, with the first lateral side and the second lateral side each formed to have a concave curvature;
- a male genital tool connected to an exterior of the housing, the male genital tool including a penis tool attached to a scrotum tool;
- an inflatable penile implant placed inside of the penis tool;
- a pump placed inside of the scrotum tool and coupled to the inflatable penile implant;
- a reservoir placed inside of the housing and coupled to the pump; and
- a lubricant placed inside of the scrotum tool, with an entirety of the lubricant outside of the pump.

12. The penile prosthesis demonstration tool of claim 11, wherein the concave curvature of the first lateral side and the second lateral side are sized to allow the housing to be positioned between adductor muscles of legs at an inner thigh location of a user.

* * * * *

UNITED STATES PATENT AND TRADEMARK OFFICE
CERTIFICATE OF CORRECTION

PATENT NO. : 10,706,744 B2
APPLICATION NO. : 15/922936
DATED : July 7, 2020
INVENTOR(S) : Taylor et al.

Page 1 of 1

It is certified that error appears in the above-identified patent and that said Letters Patent is hereby corrected as shown below:

In the Specification

In Column 4, Lines 65-66, delete "demonstration tool 30" and insert -- demonstration tool 20 --, therefor.

In Column 6, Lines 34-35, delete "demonstration tool 30" and insert -- demonstration tool 20 --, therefor.

In Column 8, Line 1, delete "pump 46" and insert -- pump 44 --, therefor.

In Column 8, Line 3, delete "pump 46" and insert -- pump 44 --, therefor.

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*